US00PP17668P3

(12) United States Plant Patent
Stahlhut

(10) Patent No.: US PP17,668 P3
(45) Date of Patent: May 1, 2007

(54) CARNATION PLANT NAMED 'CFPC MOONSTONE'

(50) Latin Name: *Dianthus caryophyllus*
Varietal Denomination: CFPC Moonstone

(75) Inventor: Roy Stahlhut, Watsonville, CA (US)

(73) Assignee: California Florida Plant Company, Salinas, CA (US)

( * ) Notice: Subject to any disclaimer, the term of this patent is extended or adjusted under 35 U.S.C. 154(b) by 199 days.

(21) Appl. No.: 11/177,865

(22) Filed: Jul. 8, 2005

(65) Prior Publication Data

US 2007/0011788 P1 Jan. 11, 2007

(51) Int. Cl.
*A01H 5/00* (2006.01)

(52) U.S. Cl. ..... Plt./274
(58) Field of Classification Search ..... Plt./274
See application file for complete search history.

(56) References Cited

U.S. PATENT DOCUMENTS

PP8,419 P 10/1993 Jessel ..... Plt./70.6

OTHER PUBLICATIONS

2001–2002 California Florida Plant Company brochure listing the varieties 'CFPC Cupid' and'CFPC Treasure'. See, e.g., pp. 3–4 (photographs).

*Primary Examiner*—Kent Bell
*Assistant Examiner*—Annette H Para
(74) *Attorney, Agent, or Firm*—Winston & Strawn, LLP

(57) ABSTRACT

A new variety of carnation plant named 'CFPC Moonstone' having large white flowers in a spray-type blooming habit.

1 Drawing Sheet

Latin name of the genus and species: Botanical classification: *Dianthus caryophyllus.*

Variety denomination: The new carnation variety denomination is 'CFPC Moonstone'.

BACKGROUND OF THE INVENTION

The present invention comprises a new and distinct cultivar of hybrid carnation botanically known as *Dianthus caryophyllus,* and referred to by the cultivar name 'CFPC Moonstone'.

'CFPC Moonstone', identified as selection no. 020550, originated from a cross made by Roy Stahlhut in a controlled breeding program in Salinas, Calif.

The female parent of the new variety is the unpatented variety known as selection no. 000132 and the male parent is the patented variety known as 'CFPC Cupid' (U.S. Plant Pat. No. 8,419). The new variety 'CFPC Moonstone' has been asexually reproduced by vegetative side shoot cuttings in Salinas, Calif. and the distinguishing characteristics are retained through successive generations of asexual reproduction.

BRIEF SUMMARY OF THE INVENTION

'CFPC Moonstone' is a potted spray-type of carnation plant variety having large white flowers.

COMPARISON WITH FEMALE PARENT

Plants of the new carnation variety 'CFPC Moonstone' are similar to the female parent selection no. 000132 in plant habit and growth rate, and compared to plants of the female parent in the following characteristics:

1. The new variety 'CFPC Moonstone' produces large white flowers and the female parent selection no. 000132 also produces white flowers.

2. The new variety 'CFPC Moonstone' has an improved flower form compared to the female parent.

COMPARISON WITH MALE PARENT

Plants of the new carnation variety 'CFPC Moonstone' are dissimilar to the male parent 'CFPC Cupid' in plant habit and growth rate. In side-by-side comparisons in Salinas, Calif. under commercial practice, plants of the new carnation variety 'CFPC Moonstone' differed from plants of the male parent 'CFPC Cupid' in the following characteristics:

1. The new variety 'CFPC Moonstone' produces large white flowers whereas the male parent 'CFPC Cupid' produces large pink flowers.
2. The new variety 'CFPC Moonstone' does not produce pollen like the male parent 'CFPC Cupid'.
3. The new variety 'CFPC Moonstone' has an improved flower form compared to the male parent 'CFPC Cupid'.

COMPARISON WITH SIMILAR VARIETIES

Plants of the new carnation variety 'CFPC Moonstone' are similar to plants of the unpatented variety 'CFPC Treasure' in plant habit and growth rate. However, in side-by-side comparisons in Salinas, Calif., under commercial practice, plants of the new carnation variety 'CFPC Moonstone' differed from plants of 'CFPC Treasure' in the following characteristics:

1. The new variety 'CFPC Moonstone' produces a better flower form and is more floriferous than 'CFPC Treasure'.
2. The new variety 'CFPC Moonstone' produces flowers without splitting of the calyx while the flowers of the variety 'CFPC Treasure' tend to split the calyx.
3. The new variety 'CFPC Moonstone' shows faster growth than 'CFPC Treasure'.

BRIEF DESCRIPTION OF ILLUSTRATION

Typical specimens of the plant and flowers for the new carnation variety 'CFPC Moonstone' are shown in the accompanying photograph. The colors shown are as true as possible within the usual limits of this kind of illustration.

FIG. 1 is a whole plant view of the new variety 'CFPC Moonstone' grown in a pot. The plant shown in the illustration is 116 days from date of planting.

DETAILED BOTANICAL DESCRIPTION

The following description of the new carnation variety 'CFPC Moonstone' is of plants 116 days from the date of planting grown in a commercial greenhouse in Salinas, Calif. in the month of December. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 12 hours. Plants are daylight neutral and flower throughout the year. Chemical growth regulators are not required for production.

The new variety may be produced as a potted spray-type carnation. To produce a commercial product the plants may be pinched once with the center bud removed. Pinched plants are about 17.5 cm tall and about 20.3 cm in diameter. Flower diameter averages about 5.7 cm with a crown of about 1.8 cm. Foliage is generally about 11.4 cm long and about 0.8 cm at the widest point. The typical container size for commercial growth is 4½ inches. It has been observed that the shelf life of the new variety is about 21 days with the first appearance of color in the buds occurring at about 100–110 days after planting of cuttings. The commercial classification of the new carnation variety is a potted spray-type.

The following description is with respect to a plant produced as a potted spray-type. The plant and flower measurements and foliage size are established as an average using standard commercial cultural practices. In the description of this new carnation variety, color values have been taken from The Royal Horticultural Society Colour Chart (R.H.S.C.C.).

PLANT

Height (cm): 18.4.
Form: Herbaceous.
Growing habit: Semi-upright.
Branching characteristics: 2–3 laterals per stem.
Breaking action: 4–5 breaks per plant with strong straight stems.
First appearance of color in buds: 100–110 days after planting.
Vigor: Excellent.
Shelf life: 21 days.
Blooming habit: Spray type.
Blooming season: Year around.
Lastingness of blooms: About 10 days.
Disease (susceptibility/resistance observed): Good resistance to soil-borne diseases such as *Fusarium oxysporum* and *F. graminearium,* and root rots such as damping off, water molds and similar types, as is typical of carnations.
Pest (susceptibility/resistance observed): None observed.
Drought and temperature (susceptibility/resistance observed): None observed.
Mutation prone: No.
Propagation:
*Type.*—Side shoot cuttings.
*Time to rooting.*—18 days with soil temperatures of 18° C. to 21° C.
*Rooting habit.*—Good fibrous system.
Growth treatments or special conditions: None.

FOLIAGE

Stem:
*Length (cm).*—14.6.
*Diameter (cm).*—0.5.
*Texture.*—Smooth.
*Cross section.*—Edged.
*Color.*—137C internode. 147D node.
Number of leaves per lateral branch: 12–14.
Arrangement of leaves: Bi-lateral along the stem.
*Shape of leaf.*—Long, narrow, lanceolate.
*Size of leaf.*—Width (cm): 0.8. Length (cm): 11.4.
*Leaf apex.*—Acute.
*Edge.*—Smooth.
*Aspect.*—Straight.
*Surface texture.*—Top: smooth. Bottom: smooth.
Leaf venation: Prominent mid-vein at underside.
Leaf longitudinal axis: Recurved.
Leaf cross section (upper side): Weakly concave.
Leaf color:
*Mature leaf, upper side*—139A. Under side: 137B.
*Young leaf, upper side.*—139A. Under side: 137B.
Leaf waxy layer: Medium.

FLOWER

Flower appearance: Matte.
Flower type: Double.
Flower profile of upper part of corolla: Convex.
Flower profile of lower part of corolla: Flat.
Flower form: Fan shape smooth petal edge with occasional irregular serrations.
Flower shape: Dome shaped, round.
Number of blossoms per branch: 10–11.
*Depth of fully expanded blossoms (cm).*—1.9.
*Diameter of fully expanded blossoms (cm).*—5.7.
Calyx:
*Sepals number.*—5.
*Length (cm).*—0.6.
*Width (cm).*—0.6.
*Color.*—Outer side: 144C outer side middle to tip: 137C. Inner side: between 157A and 148D.
*Texture.*—Smooth.
*Appearance.*—Matte.
*Shape.*—Cylindrical.
Flower petals:
*Form/shape.*—Fan shaped.
*Petal edge.*—Serrated: Width (mm): <1. Depth (mm): <1. Edge type: crenate-dentate.
*Texture.*—Smooth.
*Appearance.*—Matte.
*Petal surface of blade.*—Undulating.
*Number per flower.*—31.
*Outer petals.*—Length (cm): 4.4. Width (cm): 2.7.
*Inner petals.*—Length (cm): 3.5. Width (cm): 1.9.
Fragrance: strong sweet.
Flower bud (at onset of color):
*Length (cm).*—2.5.
*Diameter (cm).*—1.1.
*Form/Shape.*—Ovoid.

Flower color:

1. *General tonality.*—White (very pale pink hue upon opening).
2. *Petals, upper surface.*—Whiter than 155D.
3. *Petals, lower surface.*—Whiter than 155D.
4. *Petals, edge.*—Whiter than 155D.
5. *Petals, center.*—Whiter than 155D.
6. *Early bud.*—Lighter than 56D blush with striations.

Petal macule (random spots): Absent.

Flower progression with age: Slight pinkish blush quickly fades to white.

REPRODUCTIVE ORGANS

Gynoecium: Pistillate.

*Pistil number.*—1.
*Pistil length* (*cm*).3.5.
*Pistil color.*—Whiter than 155D.
*Stigma number.*—Only 2.
*Stigma color.*—Whiter than 155D.
*Stigma shape.*—Filamentous.
*Style color.*—Whiter than 155D.
*Style length* (*cm*).—2.5.
*Style number.*—Only 2.

Ovary:

*Shape.*—Ovoid.
*Surface.*—Smooth.
*Color.*—Base: 157A. Body: 144B. Apex: 144B.

Androecium:

*Stamen number.*—20.
*Stamen color.*—Whiter than 155D.
*Anther shape.*—None produced.
*Anther color.*—176C (brown, withered).
*Pollen quantity.*—None produced.

Fruit and seeds: None produced.

What is claim is:

1. A new and distinct variety of carnation plant, substantially as described and illustrated herein.

* * * * *

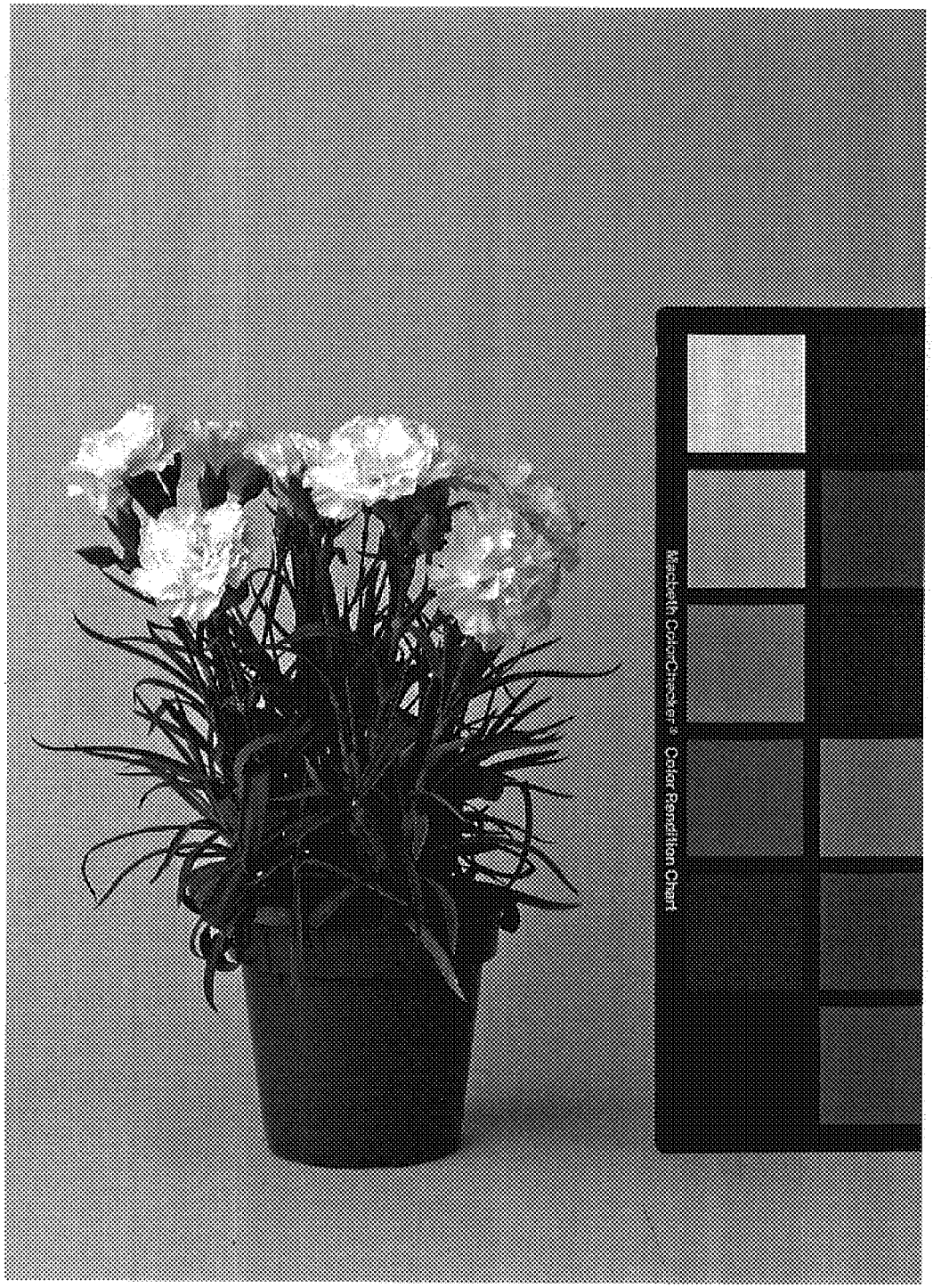
Macbeth Color Checker
Color Rendition Chart